US006795192B2

United States Patent
Dickopf et al.

(12) United States Patent
(10) Patent No.: US 6,795,192 B2
(45) Date of Patent: Sep. 21, 2004

(54) SPR SENSOR AND SPR SENSOR ARRAY (75) Inventors: Stefan Dickopf, Heidelberg (DE);
Kristina Schmidt, Heidelberg (DE);
Dirk Vetter, Heidelberg (DE)

(73) Assignee: Graffinity Pharmaceutical Design GmbH, Heidelberg (DE)

(*) Notice: Subject to any disclaimer, the term of this patent is extended or adjusted under 35 U.S.C. 154(b) by 152 days.

(21) Appl. No.: 10/223,010

(22) Filed: Aug. 19, 2002

(65) Prior Publication Data
US 2003/0128364 A1 Jul. 10, 2003

Related U.S. Application Data (63) Continuation of application No. PCT/EP01/01793, filed on Feb. 16, 2001.

(30) Foreign Application Priority Data
Feb. 22, 2000 (DE) .......................................... 100 08 006

(51) Int. Cl.[7] ............................................... G01N 21/55
(52) U.S. Cl. ...................................................... 356/445
(58) Field of Search .............................. 356/445, 318, 356/244, 246; 422/82.05–82.08

(56) References Cited

U.S. PATENT DOCUMENTS

| 4,931,384 A | 6/1990 | Layton et al. |
| 5,313,264 A | 5/1994 | Ivarsson et al. |
| 5,485,277 A | 1/1996 | Foster |
| 5,779,978 A | 7/1998 | Hartmann et al. |
| 5,792,667 A | 8/1998 | Florin et al. |
| 5,858,799 A | 1/1999 | Yee et al. |
| 5,917,607 A | 6/1999 | Naya |

FOREIGN PATENT DOCUMENTS

| DE | 196 15 366 | 10/1997 |
| DE | 198 14 811 | 8/1999 |

(List continued on next page.)

OTHER PUBLICATIONS

Striebel, C., et al., "Characterization of biomembranes by spectral ellipsometry, surface plasmon resonance and interferometry with regard to biosensor application". Biosensors & Bioelectronics 9, 139–146, (1994).

(List continued on next page.)

Primary Examiner—Michael P. Stafira
(74) Attorney, Agent, or Firm—Nath & Associates PLLC; Marvin C. Berkowitz; Derek Richmond (57) ABSTRACT

The invention relates to an an SPR surface plasmon resonance spectroscopy sensor for parallel measurement of a plurality of samples, comprising a body (1a) having several SPR sensor areas (2) for guiding radiation in order to carry out SPR measurements and which are coated with a material which is suitable for SPR in such a way that each SPR sensor area (2) can be exclusively associated with a single sample. The radiation conducting body (1a) forms a unit with the SPR sensor areas (2), whereby the path of the rays guided by the SPR sensor areas (2) can also extend through the radiation conducting body (1a).

52 Claims, 8 Drawing Sheets

FOREIGN PATENT DOCUMENTS

| | | |
|---|---|---|
| DE | 199 23 820 | 1/2000 |
| DE | 199 55 556 | 6/2000 |
| EP | 0 286 195 | 10/1988 |
| EP | 0 341 928 | 11/1989 |
| EP | 0 388 874 | 9/1990 |
| EP | 0 971 226 | 1/2000 |
| EP | 0 973 023 | 1/2000 |
| WO | WO 90/05295 | 5/1990 |
| WO | WO 90/05305 | 5/1990 |
| WO | WO 94/16312 | 7/1994 |
| WO | WO 95/22754 | 8/1995 |
| WO | WO 97/15819 | 5/1997 |
| WO | WO 98/32002 | 7/1998 |
| WO | WO 98/34098 | 8/1998 |
| WO | WO 99/30135 | 6/1999 |
| WO | WO 99/41594 | 8/1999 |
| WO | WO 99/56878 | 11/1999 |
| WO | WO 99/60382 | 11/1999 |
| WO | WO 00/31515 | 6/2000 |

OTHER PUBLICATIONS

Kumar, Sanj, et al., "Small Molecule Drug Screening Based on Surface Plasmon Resonance". Chapter 8 from "Advances in Drug Discovery Techniques", Harvey, Alan L., ed., John Wiley & Sons Ltd., London (1998).

Zizlsperger, M., et al., "Multispot parallel on–line monitoring of interracial binding reactions by surface plasmon microscopy". Progr. Colloid Polym. Sci., 109, 244–253, (1998).

Nelson, Bryce P., et al., "Near–Infrared Surface Plasmon Resonance Measurement of Ultrathin Films. 1. Angle Shift and SPR Imaging Experiments". Analytical Chemistry, 71, 3928–3294, (1999).

SPR SENSOR AND SPR SENSOR ARRAY

This application is a Continuation of PCT/EP01/01793 filed Feb. 16, 2001, the entire contents of the application which is hereby incorporated in its entirety.

FIELD OF THE INVENTION

The present invention relates to providing SPR sensors capable of assaying a plurality of samples simultaneously, methods for their production, measuring assemblies for scanning the sensors in accordance with the invention in parallel as well as to their use in the search for active agents and in high-throughput screening (HTS).

BACKGROUND OF THE INVENTION

Continuing progress in automating the search for active agents has resulted in the question of miniaturization and parallelization gaining ever-increasing interest. Miniaturizing sample containers and the apparatus used in synthesis causes a plurality of substances to be assayed in ever-decreasing volume. This is why it is necessary in achieving novel detector and sensor systems to configure them so that several measurements can be run simultaneously in parallel, or a large number of samples assayed in sequence in shortest time whilst minimizing the volume of the substance needed therefor (high-throughput screening). Salient to this is enhancing the degree of automation.

There is furthermore a need to provide also the sensors used for analysis in a parallel and miniaturized format so that assaying a plurality of samples in shortest time and with minimum volume and consumption is achievable in thereby boosting the throughput of the substances to be characterized.

One highly sensitive measurement method for boundary layer characterization is known which is termed surface plasmon resonance (SPR) spectroscopy in pertinent literature. This method is based on optical excitation of surface plasmons along the boundary layer of films of metal.

It is usual in this arrangement to detect the light reflected by a thin gold film. When the condition for resonance is suitable (angle of incidence and wavelength of the light and film thickness of the gold film) the intensity of the reflected light decreases. In absorption of the light, excitation of the charge density waves of the electron gas occurs at the gold surface. These charge density waves are called plasma oscillations, their quantized excitation states plasmons.

To observe the resonance there are two methodic approaches. Either use is made of monochromatic light and the intensity of the reflected light is recorded as a function of the angle of incidence, or the angle of incidence is maintained constant and the wavelength of the light is varied. In both cases there is a shift in the location of resonance when the refractive index of the medium changes on the side of the gold film facing away from the incident light.

These methods are described in prior art as detailed, among others, by Striebel, Ch; Brecht, A; Gauglitz, G in Biosensors & Bioelectronics 9 (1994), 139-146. The resonance conditions for surface plasmon excitation greatly depend on the optical properties of the dielectric surrounding the metal film. Determining the refractive index or film thickness of thin dielectric films is basically possible with high accuracy by known prior art.

SPR spectroscopy is finding increasing application e.g. in biochemical analysis by making it possible to assay the interaction between partners (for example in the biomolecular reactions of antibodies and antigens) directly and without marking. For this purpose, an interaction partner (e.g. ligand) is immobilized on the surface of the metal, the other interaction partner (e.g. analyt) directed in solution over the surface. The interaction can be directly verified as the increase in film thickness via the change in the refractive index.

One task often involved in the miniaturization and parallel measurement of many samples is bringing the sensor sites into contact with fluid without, for example, cross-contamination occurring.

In the search for active agents conventional SPR sensors employ a prism coated with a thin film of metal. The sample to be assayed is brought into contact with the metal or the modified metal surface, and the SPR reflection spectrum of the sample is measured by coupling light into the prism and measuring the intensity of the reflected light as a function of the angle of incidence (cf. Chapter 8, "Small Molecule Drug Screening based on Surface Plasmon Resonance" in *Advances in Drug Discovery Techniques*, John Wiley & Sons Ltd, London 1998).

A parallel approach to analyzing a sample array is SPR microscopy (SPM) (see e.g. EP 388 874 A2 or M. Zizlsperger, W. Knoll, Progr. Colloid Polym. Sci. 1998, 109, pp. 244-253) involving coating various sites on various samples of a gold surface applied to a prism and obtaining an image of the gold surface at the SPR angle on a CCD chip. During the measurement the angle is altered by a mechanical scanner. This method is, however, restricted to objects of small diameter.

A more recent SPR method is disclosed in WO 94/16312 A1 in which detecting the binding of small amounts of substance is achieved by optical fibers partially coated with a gold film. However, here too, the problem still exists in designing a sensor array required to assay a plurality of samples in parallel in accordance with this principle. Such an array of gold-coated fibers is, on the one hand, expensive and highly sensitive to mechanical stress, and, on the other, producing the array in parallel as proposed therein is difficult to achieve technically.

Optical fibers are also employed as it reads from WO 98/32002 A1. To protect them from being damaged physically the fiber cable is housed in a pipette. To achieve an array it is proposed to use a series arrangement of such pipettes. However, miniaturizing such an arrangement is difficult to achieve, especially for parallel measurement of many different samples.

WO 97/15819 A1 describes a dual-channel sensor comprising an objective mount as used in microscopy. Supplying fluid to the gold sensor site is achieved with the aid of a flow-through cuvette. Such a configuration is complicated especially in miniaturized HTS.

Known from U.S. Pat. No. 5,485,277 is a SPR sensor array using a waveguide configured so that multiple reflection occurs therein in thus simplifying signal analysis. Several spatial channels, e.g. a sensor channel and a reference channel, are employed in the measurement. There is no mention, however, of how the separate channels are generated.

Known from DE-196 15 366 A1 is a method and a means for simultaneously assaying a plurality of samples e.g. in a matrix arrangement. Separating the samples is done by applying the samples spatially separated.

WO 99/41594 describes a SPR system in which for a better time resolution the material properties of sites bordering a full-size SPR-sensitizing coating are modified to permit determining the intensity of the radiation reflected by the surface resolved in time or space.

WO 90/05295 describes a SPR system comprising a plurality of sensor surfaces. The SPR sensor system consists of a plate of glass coated with a film of metal, covered in turn by a dielectric film. The ligands making measurement possible are applied to the dielectric film. Separate sensor sites are generated by the separate application of the ligands.

A further possibility of simultaneously assaying a plurality of samples is described in WO 99/60382 A1 from which the preamble of the present claim 1 is known. In the arrangement as described several strip-type lightguides are arranged at a defined spacing on a planar backing and provided with a thin film of metal to permit excitation of such plasmons, whereby means are provided which separate the sensitized sites of the individual thin metal films by interruption thereof such that each lightguide can be assigned one sample only.

The lightguide described in WO 99/60382 A1 is fixed to a backing plate. This necessitates very high precision in production. The light-guiding film is deposited in a separate coating step. There is a risk of inhomogeneities materializing from one sensor to the other. Should solvent gain access to the interlayer between backing and light-guiding film problems may be encountered in the bonding of the deposited film.

OBJECTIVE OF THE INVENTION

The present invention is based on the objective of providing SPR sensors which are preferably planar, and measuring assemblies having a simpler configuration, as well as on methods for production thereof which are more cost-effective than those of known prior art in permitting simultaneous assaying of a plurality of samples. More particularly the invention is intended to create SPR sensors which include a light-guiding film containing at least two sensor surface areas as well as providing an array of at least two SPR sensors in avoiding the disadvantages of WO 99/60382 A1.

SUMMARY OF THE INVENTION

This objective is achieved by the characterizing features of claim 1 and by the subject matter of the parallel claims. Preferred aspects are described in the sub-claims.

In accordance with the invention there is now provided for an SPR sensor suitable for assaying a plurality of samples in parallel a self-supporting pattern in which a substrate backing SPR sensor sites is itself radiation-conductive and itself contributes towards beaming the radiation for SPR assaying.

Radiation in this sense is understood to be any radiation, especially electromagnetic radiation, in the range IR to visible suitable for excitation of plasmons. This radiation as preferred is sometimes also simply referred to as light without inferring any restriction to visible light, however.

The configuration of an SPR sensor in accordance with the invention overcomes the disadvantages of prior art (more particularly of WO 99/60382 A1) as regards the production problems since a plurality of radiation-conductive SPR sensor sites can now be provided in a single sensor without a separate backing needing to be provided. This not only simplifies production of the SPR sensor in accordance with the invention, but also results in SPR sensors which are more compact than known generic sensors. This facilitates, among other things, integrating a plurality of SPR sensors into a SPR sensor array.

As compared to prior art as set forth in DE-196 15 366 A1, U.S. Pat. No. 5,487,277, WO-99/41594 or WO-90/05295 the present invention features the difference and advantage that the SPR sensor sites are now separated by an interruption in the SPR-sensitzing film, resulting in a clear and explicit separation of the discrete sample sites right from the start with no need to use complicated ligand or sensing material coating techniques.

Making use of sensors or sensor arrays in accordance with the invention now makes it possible to assay as a function of the angle of incidence, which due to the small dimensions cannot be implemented with a lightguide in principle.

Although the SPR sensors in accordance with the invention can be assembled from initially separate SPR sensor sites and a body, the SPR sensors are preferably produced starting with a sole radiation-conductive substrate in which SPR sensor sites are formed which feature a SPR-compatible or SPR-sensitizing surface coating of suitable thickness (e.g. platinum, gold, silver, aluminum, copper, nickel or suitable alloys thereof) with the addition of an intermediate film promoting bonding (e.g. chromium) where necessary. These SPR sensor sites formed in the substrate into which radiation can be coupled and by which the radiation can be conducted for surface plasmon excitation in the SPR film and for communicating the modified radiation to an analyzer (i.e. modified by the SPR effect, in other words a reduction in intensity as a function of the wavelength or angle concerned as an indication of the dielectric properties of the outer side of the SPR film) are separated by separating means so that the radiation stemming from separated SPR sensor sites can be detected separately. These separating means also ensure that each SPR sensor site can be assigned a sample to be assayed, i.e. with no cross-contamination of neighboring SPR sensor sites.

In accordance with a first basic configuration the separating means are formed by depositing protuberances on the surface of the substrate. These are located between the SPR films, the substance from which the protuberances are made being selected so that no spreading of radiation occurs in the regions of the substrate between the SPR sensor sites, e.g. by such radiation being absorbed by this substance. For this purpose, the refractive index of the substance needs to be suitably selected to prevent a total reflection in the intermediate regions and the substance needs to have an absorbing or damping effect for the radiation. When the substrate is made of glass, e.g. silicon or a silicon compound is suitable for this purpose. In addition, the protuberances need to be selected so that they represent a fluid barrier so that no cross-contamination between neighboring samples or sensor sites occurs.

As evident, in this first basic configuration the substrate itself forms the backing for the SPR sensor sites because these and the separating areas are integral components of the substrate which remains unchanged in its volume. It is merely the surface that is changed in defining the corresponding sensor sites or separating areas in the interior of the substrate. Accordingly, all and any conduction or guidance of radiation takes place in both the sensor sites and in the backing or substrate.

In accordance with a second basic configuration the separating means are formed by cut-outs in the material of the substrate between the SPR sensor sites. These cut-outs can be formed by any suitable technique, e.g. by sawing, milling, etching etc. This results in the SPR sensor sites forming fingers protruding from the remaining original substrate which in turn forms the backing for the sensor sites. These fingers are, however, connected to the remaining substrate or backing radiation-conductively and the radiation coupled into the sensor sites also passes through the backing. The second basic configuration has the special advantage that the protruding fingers, representing SPR sensor sites, can be arranged in a suitable matrix and such SPR sensors on a suitable matrix can be composed into sensor arrays capable of cooperating with multiwell plates of corresponding format in thus creating particularly effective SPR sensor arrays for high-throughput screening.

BRIEF DESCRIPTION OF THE DRAWINGS

Further features, properties and advantages of the present invention are described in the following detailed description of preferred aspects with reference to the drawings in which.

DETAILED DESCRIPTION OF ASPECTS OF THE INVENTION

Figure 1:
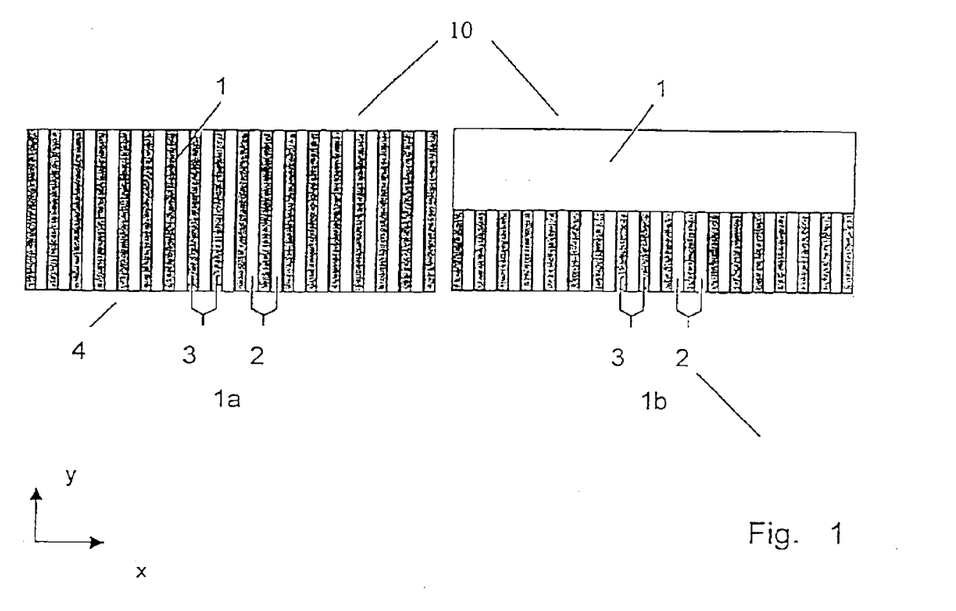
FIG. 1a shows one variant of the first basic configuration of a sensor in which the length of the surface coating of the SPR material and separating material runs along the full height of the sensor.
FIG. 1b shows another variant of the first basic configuration of a sensor in which the length of the coating of the SPR material and separating material does not run along the full height of the sensor.

Referring now to FIGS. 1a and 1b there are illustrated various aspects of the first basic configuration of a sensor 10 in accordance with the invention consisting of an optical light-guiding film 1 or, in general, a radiation-conductive substrate 1 fabricated of a uniform material. To simplify the description the dimension along the x axis as shown is termed width, the dimension along the y axis as shown is termed height and the dimension perpendicular to the plane x-y (plane of the drawing) is termed thickness.

The substrate 1 incorporates sensor surface areas 2 separated by portions 3 ensuring a regular center-spacing.

Preferably, the surface areas 2 and 3 are configured strip-shaped in parallel on an equal center-spacing, as shown. The sensor surface areas 2 consist of a SPR-sensitizing film, preferably a metal film of platinum, silver, aluminum, copper, nickel, particularly preferred being a film of gold. In addition, a film promoting bonding (not shown), e.g. a film of chromium or titanium, should be included between the light-guiding film or substrate and sensor film. The separating portions 3 separate the sensor surface areas in preventing cross-contamination when fluid is brought into contact with a sensor surface area. This is achieved e.g. by configuring the separating portions 3 as protuberances, as evident from the view in perspective of FIG. 2d or the cross-sectional view of FIG. 3. The portion 3 serves furthermore to absorb the light which is not reflected by the sensor surface area. For this purpose the material of the separating portions 3 should have a refractive index as compared to the refractive index of the substrate material which is suitable in avoiding total reflection at the interface whilst permitting absorption. This results in a beam path as shown diagrammatically in FIG. 2d. In FIG. 2d for detecting the radiation suitable for SPR, e.g. in the visible wavelength range, incident radiation is from underneath, and at the end opposite thereto radiation emerges singled in accordance with the SPR sensor sites in thus permitting separate analysis of the exit radiation from the various sensor sites.

In FIG. 1a sensor surface areas 2 and portions 3 take up the full height of the sensor 10. In FIG. 1b only part of the full height is made use of in each case. It is just as possible that the portions 3 take up the full height and the sensor surface areas only part of the height of the light-conductive material (not shown). It is also not necessary that all strips of a material have the same height. However, the height of the separating means should amount to at least the height of the sensor sites.

Figures 2A, 2B, 2C:
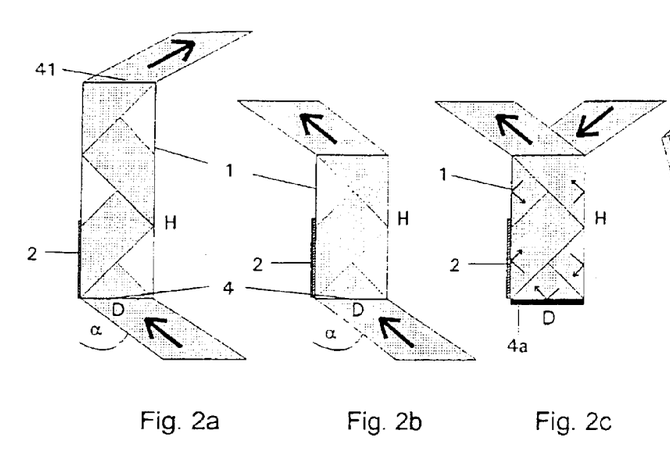
FIGS. 2a and 2b are each a diagrammatic illustration of the beam path of the radiation in which the surface areas for entry and exit of the light lie on opposite sides of the SPR sensor site.
FIG. 2c shows the beam path of the radiation in which the entry surface area is identical to the exit surface area.
Figure 2D:
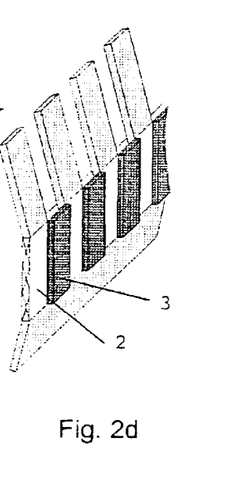
FIG. 2d is a diagrammatic view in perspective illustrating the effect of the sensor sites and separating areas.

Referring now to FIGS. 2a–2c there are illustrated various possibilities for guiding the light in the sensor sites shown as a side view in FIG. 1b. The light is beamed into the entrance window 4 of the sensor strip 1, whose surface area stands perpendicular to the sensor surface area 2, and guided within the light-conductive film 1 by means of total reflection. In the case as shown in FIGS. 2a and 2b it exits from the side opposite the entrance window 4, i.e. via the exit window 41. In this arrangement the excitation light is also reflected by the sensor surface area 2. When the number of reflections is even, the light emerges parallel offset from the sensor strip 1, and when the number is odd mirror-inverse thereto to the side of light incidence. The angle of incidence α should furthermore be selected so that the light beam emerges only on one side and the SPR effect is optimally induced. Another case is shown in FIG. 2c. Here, the light is coupled into and from the same window 4. To make this possible, the side of the sensor identified 4a is mirror-coated so that the light is reflected and re-exits through the entry window.

The material of the substrate 1 can be selected from any glass or polymer (e.g. polycarbonate, PMMA, ORMOCER®) having a sufficiently high optical transparency in the range of visible light up to the near infrared. Preference is given to a glass such as borosilicate or optical glass in general because the optical surface quality and the medium has less schlieren and lower dispersion properties than conventional plastics. Apart from this, glasses excel by having a high resistance to chemicals and a low unspecific protein adsorption important for biosensors.

The refractive index of the material should preferably be in the range 1.46 to 1.58 where gold is used as the SPR-sensitizing film to permit measuring the SPR signal in a solution with the refractive index between 1.33 and 1.37.

The thickness D of the sensor or substrate 1 is required to permit propagation of the light in the sense of modal propagation as well as geometric optical beaming of the light, preference being given to a thickness D in the range 0.1 mm to 5 mm. As a minimum the sensor strip 1 may feature a height H exclusively permitting reflection at the sensor surface area 2 or having the dimension of the sensor surface area 2. Specifying a maximum to the height will depend on the desired mechanical stability of the strips. H and D are to be adapted so that with the desired number of reflections an angle conducive to SPR is attained. Although there is no need for an additional backing film, this may be applied as a supplement.

Figure 3:
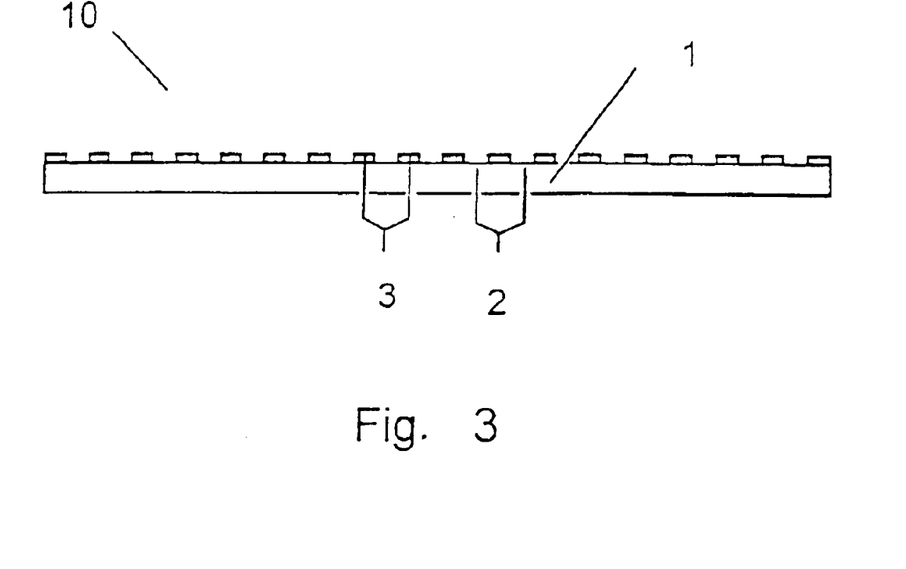
FIG. 3 is a cross-sectional view of a sensor in a first basic configuration.

To prevent crosstalk in spotting the discrete sensor surface areas, the separating portion may be configured by a covering film forming protuberances 3—as shown in FIG. 3—in the form of a fluid barrier. The covering film should moreover have an absorbing effect to ensure divisioning of the surface excitation in the discrete sensor surface areas by extinction of the light in the areas between two sensor sites. Accordingly, the material of the covering film needs to be highly absorbing optically as regards the incident light and stable chemically to the reagents and solvents used. Furthermore, structuring must be possible by known microfabrication techniques for producing covering films having a width preferably in the range 0.01 to 10 mm, more particularly 0.1 to 1 mm.

Figure 4A:
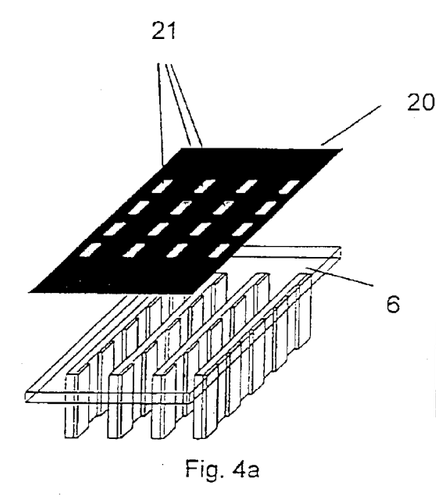
FIGS. 4a and 4b show each possible arrays of sensors in accordance with the first basic configuration.
Figure 4B:
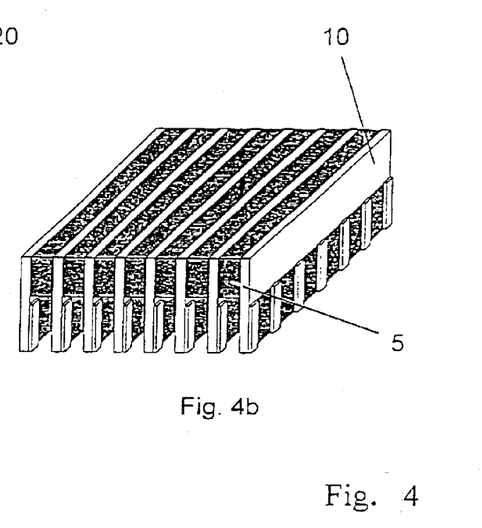

Referring now to FIGS. 4a and 4b there is illustrated how the discrete sensors can also be arrayed in two examples, possibly involving a large number, preferably 10 to 100,000 sensor sites arranged in parallel to each other on a defined center-spacing.

Measuring assemblies for scanning such sensor arrays as a function of the wavelength in parallel are described in DE 199 55 556.7, to the disclosure content of which reference is herewith made and including the content thereof.

Simultaneously sensing the SPR effect as a function of the angle of incidence in all sensor sites in such an array is highly complicated as regards the hardware requirements. But doing this for discrete sensors in parallel by means of a suitable lightguide is easy, as described further on.

Referring now to FIG. 4a there is illustrated how for forming a SPR sensor array a plurality of planar sensors 10 are arrayed by bonding the sensors to the light exit side with a transparent covering plate 6. The adhesive used for this purpose needs to be transparent in the range of visible light to near infrared or generally transparent as regards SPR radiation and to feature a refractive index similar to that of the glass used for the sensors 10 and covering plate 6 ("similar" in this sense being with a difference of max. 10%). In making an array of the sensors, care needs to be taken to ensure that the planar, plate-type sensors are located planoparallel to each other.

Since there are no light-absorbing portions between the sensor strips in this arrangement, it is necessary to mask the excitation light passing between two sensors when the sensor array is exposed as shown in FIG. 2d. For this purpose a perforated mask 20 is mounted on the array having perforations 21 only where the exit windows are located in thus masking the light not coming into contact with the sensor sites.

Referring now to FIG. 4b there is illustrated how sensors are arrayed in making use of intermediate elements or spacers 5.

The sensors are arranged spaced away from each other at the desired center-spacing by spacers of a defined thickness and compressed or bonded to each other after being compressed. The spacers 5 have the task of masking light which is not coupled into the sensors.

The side surface areas of the spacers need to be fabricated planoparallel to each other, however, to guarantee that no wedge error materializes from one sensor to the next when the sensors 10 and spacers 5 are stacked. This is why use should be made of a material producing no mechanical stress, preferably the same material as the substrate of the sensors.

Where use is made of glass or some other material transparent to the radiation as the material for the spacers, the ends of the spacers must be additional provided with a light-absorbing film which guarantees that no light can gain access through these spacers to the detector.

Using an adhesive for fixing the array after stacking requires a choice of compatible materials for sensor and adhesive. The refractive index of the adhesive must be smaller than that of the sensor material so that light in the sensor can be guided by means of total reflection.

Introducing the adhesive into the gaps between sensors and spacers can be done by means of capillary action in thus enabling the array to be stacked in a first step and the sensors located relative to each other with the adhesive in a second step.

If the sensors are merely clamped in place, the remaining air gap also permits total reflection of the light beamed thereinto.

Arraying a plurality of sensors requires the sensors to be precisely located relative to each other, since this is necessary for optically coupling the parallel light into and out of the array at a defined angle.

The spacing between two sensor sites or sensors dictates the volume needed for the application and should be a minimum, preferably in the range 0.1 mm to 10 mm. After assaying, the sensor array is removed from the sensing solution. If the sensor to sensor spacing is a capillary gap the fluid can be suctioned off with a porous material, centrifuged away or blown off by compressed air into a catchment vessel. Larger gaps will drain by themselves.

Methods for the production of sensors in accordance with the first basic configuration involve a plurality of steps. In a first step the light-absorbing portions can be produced between the sensor surface areas on the light-guiding film before or after machining the ends for coupling in the light. For this purpose a film permitting photostructuring can be used which is deposited on the light-conductive substrate and patterned by means of photolithographic techniques, thus exposing areas in a predefined matrix. A backing plate which is transparent in the aforementioned light ranges and corresponding in height to the length of strips of the light-conductive substrate is coated with a homogenous film of photoresist which as the (covering) coating can be patterned in UV light and absorbing in the range of visible and/or infrared light. This resist is exposed by means of a photomask, developed and cured. After this, this plate is cut into a plurality of strips or substrates 1, the ends of which are subsequently optically polished. The height of the strips is determined in each case by the number of reflections used for SPR assaying. After the ends have been polished the strips are coated with an SPR-sensitizing film, such as gold.

Substrates may also be used which already feature the desired length and whose ends are polished and having received the light-absorbing ridges individually produced by one of the techniques as cited above. Here too, coating the result with the SPR-sensitizing metal film is done in a last working step.

Furthermore, use may be made of screen printing techniques which deposit the light-absorbing film on the light-conductive material only in the windows of the screen printing mask. Likewise, a prepatterned cover including windows corresponding to the sensor sites may be applied to the material by means of bonding or some other jointing method. The free areas produced by these methods are first provided in a subsequent step with a film promoting adhesion, preferably a thin metal film. By means of sputtering or vacuum deposition a thin SPR-sensitizing film, for example of gold, is deposited, before which a film promoting adhesion is applied which needs to be thinner (e.g. a magnitude thinner) than the SPR-sensitizing film so that SPR resonance is influenced as little as possible. The light-absorbing areas can be included in the coating with no change to the functions as described above, because the light fails to penetrate as far as this film. In other words, the light-absorbing areas are preferably used as masks in depositing the SPR-sensitizing film.

The generated sensor sites are arranged to advantage in a matrix corresponding to the currently popular multiwell plate formats, a multiple or a whole number divided measure thereof relative to each other. This permits spotting with fluid, for example containing samples, from multiwell plates by means of fluid transfer hardware on to the sensor surface areas rendered incapable of cross-contamination by the presence of fluid barriers.

Referring now to FIGS. 4a and 4b there is illustrated how individual sensor strips are combined into a sensor array providing m×n sensor sites by combining m sensors of light-conductive substrate with n sensor surface areas. The sensors are arranged spaced away from each other in a defined center-spacing by spacers 5 and compressed or bonded together, or fixed in place by means of a covering plate 6, for example by bonding.

The discrete sensors of the lightguides as shown can be brought into contact with the fluid with the aid of robotic pipetting devices or other means of fluid transfer, before being arrayed. For this purpose it is necessary to lay the sensors, this involving spotting the sensor surface area with fluid, for example from multiwell plates containing in each well another solution. In one preferred embodiment up to 96 sensor surface areas can be produced on a 120 mm wide sensor. Further miniaturization is possible by making use of the cited microfabrication techniques.

Figure 5A:
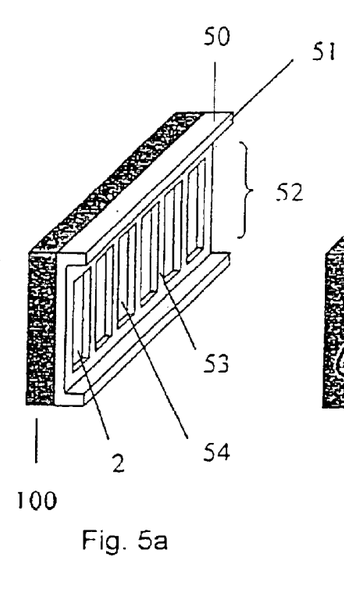
FIGS. 5a and 5b show each further possible embodiments of a sensor and a corresponding sensor array.

Referring now to FIG. 5a there is illustrated a further variant in which discrete sensors 100 are produced, additionally incorporating a spacer 50. The light-absorbing fluid barrier spacers are produced in a second material and fixedly connected to the light-conductive substrate. In this example a wafer of silicon is patterned so that in a first portion 51 spacers materialize and in a portion 52 setback from the latter, open portions 54 materialize which window the sensor regions and likewise protuberances or ridges 53 materialize serving as fluid barriers. The patterned silicon wafer featuring a plurality of replicas of the light-conductive strips required is bonded to the light-conductive substrate and subsequently this composite is divided into strips or plates and the ends are polished. The last step is depositing the SPR-sensitizing film directly on the light-conductive substrate through the windows. Here again separating means serve as the mask.

Figure 5B:
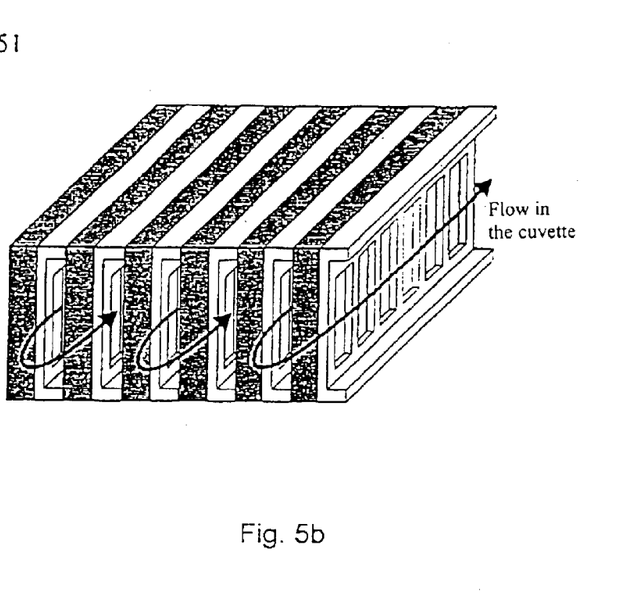

Referring now to FIG. 5b there is illustrated an array of such sensors 100, starting from discrete sensors 100 which are interconnected so that capillary gaps located between the sensors 100 are connected to each other in a meander configuration and which can be filled by an external pump and re-discharged. In this case the sensor regions on the sensor 100 need to be coated in a first step with the samples to be assayed and then a plurality of strips joined together by compression or bonding into a kind of "flow-through cuvette".

Figures 6, 6A, 6B:
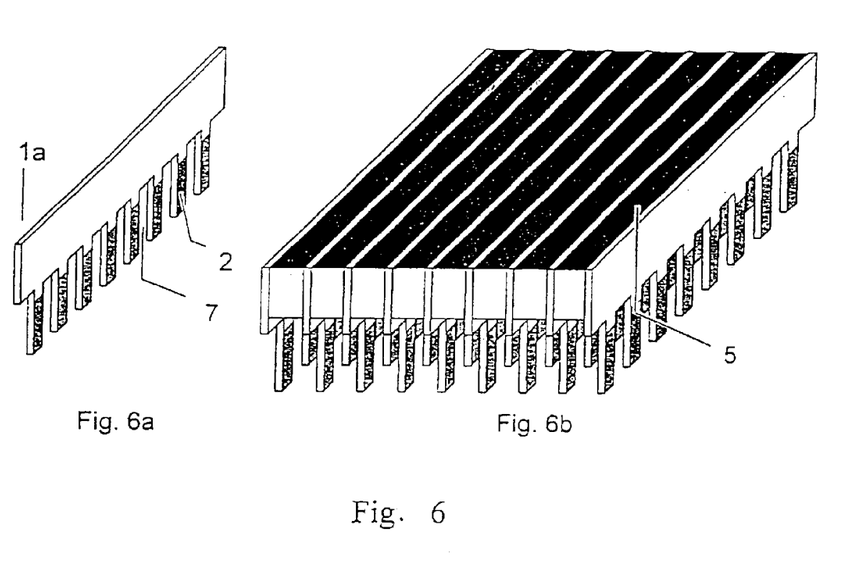
FIG. 6a shows a sensor in accordance with a second basic configuration.
FIG. 6b shows a possible array of a plurality of sensors as shown in FIG. 6a, FIG. 7a is a diagrammatic illustration of one possible variant of a measurement assembly for assaying as a function of the angle of incidence.

Referring now to FIG. 6a there is illustrated a particularly preferred embodiment as an example for the second basic configuration in which the separating portions 3 are generated by cut-outs 7. In this arrangement use is made likewise of planar, transparent substrates for producing both a sensor with a plurality of sensor sites and an array thereof.

In this case the sensor surface areas are not separated by a light-absorbing material, but spatially directly by material being removed between two sensor sites 2. This is achievable both by some method of removal, such as for example sawing or milling and laser machining or by any of many different etching techniques, depending on the nature and thickness of the material concerned.

The result is a backing 1a from which the sensor sites 2 protrude like fingers.

One particularly preferred embodiment of a sensor array is shown in FIG. 6b which is produced similar to the arrays as shown in FIGS. 4a and 4b in making use of sensors as shown in FIG. 6a.

FIGS. 6a and 6b show arrangements of several sensors in the shape of a comb. The special geometry of the fingers makes it very simple to coat gold sensor surface areas on the fingers. The center-spacing of the fingers preferably corresponds to that of the matrix of a 1536-type multiwell plate and the cut-outs are dimensioned so that the fingers of the sensor or sensor array dip into the wells of the multiwell plate. This enables the fingers to be coated both before and after stacking the sensor strips into an m×n array, since in this case each sensor surface area is spatially separated from its neighbor and thus each sensor region can be dipped into a well. Preferably each sensor region can be coated with a variety of ligands, assaying then preferably being done with a sole analyte, although it is just as possible to present a variety of analytes, for example, in the wells of a multiwell plate and to present only one ligand.

It is also possible to combine the first basic configuration and second basic configuration, namely in a further embodiment (not shown) of a sensor containing spacers defined by both recesses and coverings. Thus, it is possible, for example, that a sensor has sensor sites which are separated alternatingly by recesses and coverings, it being likewise possible to form a comb-like structure with cut-outs as shown in FIG. 6a, the individual fingers then in turn being subdivided namely by coverings.

Although the sensors as shown in the Figs. all feature sensor sites in parallel and on the same center-spacing, as is preferred, it is just as possible to achieve other structures. Thus, more particularly the spacing and/or width of the sensor sites may vary from one sensor site to the next, e.g. in such a way that a certain number of narrow sensor sites are separated from each other by narrow recesses to form a group separated by recesses from other groups of the same kind which are wider than the narrow recesses within a group.

A discrete sensor or also an array thereof is exposed with a beam of parallel or focused light. As long as the light is not irradiated near perpendicular into the sensors, only the light beamed into the sensor strips by the ends of the fingers or sensor sites enters into the sensor. In the light-guiding film the light is reflected at the sensor surface areas. Under suitable conditions of resonance a charge density wave is configured along the boundary layer between gold and fluid and the intensity of the reflected light is diminished. The wavelength or angle function of the intensity of the reflected light permits characterization of a fluid brought into contact with the sensor.

The light coupled into the sensor exits the sensor after at least one reflection at the sensor surface area and is then imaged on a detector unit (Det, e.g. CCD camera) for analysis. Light which was not coupled into the ends of the SPR sensor sites 2 or having materialized by edge dispersion is practically "blocked" by the spacers 5, 50 or covering 6 or it is reflected in directions which are not "seen" by the detector. At the light exit side of the sensors, beams of light emerge at the locations under which a sensor surface area is to be found, no light emerging from the intermediate regions (FIG. 2d).

Figure 7A:
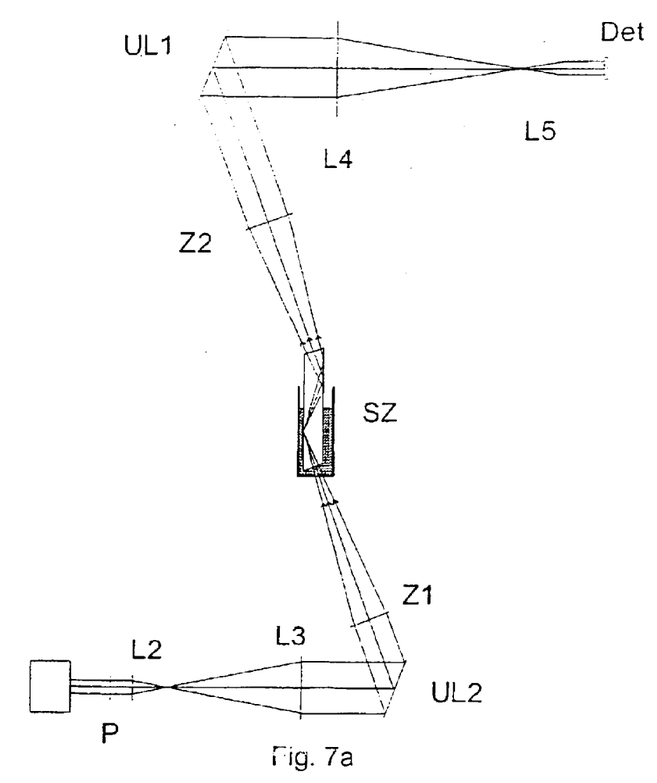

Apart from transluminating the sensor strips with parallel light, as already indicated in FIGS. 2a–2d, and measuring the transmitted or reflected intensity as a function of the wavelength, the sensors can also be beamed with the light focused to measure the transmitted intensity as a function of the angle of incidence, as will now be described with reference to FIGS. 7a and 7b.

Figure 7B:
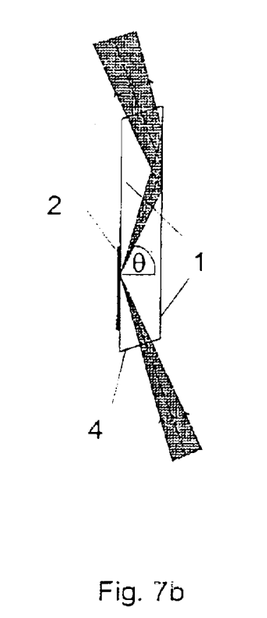
FIG. 7b is a detail on a magnified scale of the beam path within the light-guiding film as shown in FIG. 7a, and FIG. 8 is a diagrammatic illustration of a possible variant of a measurement assembly for assaying as a function of the wavelength.

Referring now to FIG. 7b there is illustrated how a beam of light focused by a suitable focusing means enters the light-guiding film 1 through the entrance window 4 and is reflected internally by the active sensor film 2 on which the focal point of the beam is located. After this reflection the beam again becomes divergent and exits from the light-guiding film. The length and number of reflections need to be restricted in this embodiment so that the cross-section of the divergent light beam is not wider than the exit window of the light-guiding film. Advantageously, the entrance and exit windows in this method of exposure should form a small angle to the normal of the sensor so that the central core of the light beam on entering and emerging is not refracted, the verges and central core of the beam then remaining symmetrical.

Measuring the intensity along the cross-section of the exit light beam permits detecting the incidence angle function of the intensity of the reflected beam. For this purpose a measuring assembly as shown in FIG. 7a, for instance, may be used wherein the light of a collimated monochromatic light source in the red or near infrared spectral range (e.g. HeNe laser or diode laser) is selected by means of the polarizer p firstly in accordance with TM polarization as regards the reflection at the sensor layer. Then, lenses L2 and L3 are used to spread the light into a parallel beam, the cross-section of which is required to correspond to at least the width of the sensor (not shown in this Fig. since the sensor protrudes into the plane of the drawing). Via deviating mirror (UL1) and a barrel lens Z1 of suitable focal length as the focusing means a parallel beam focused in the plane of the drawing and perpendicular to the plane of the drawing is generated, in thus making it possible to expose all sensors protruding into the plane of the drawing and to produce a focal point at the same level within each sensor site of the sensor.

The mean angle Θ is required to roughly correspond to the angle at which SPR resonance is observed. The aperture angle of the beam amounts to a few degrees to cover an angular range sufficient for the anticipated shift in the resonance. Following internal reflection at the gold film the beam is again fanned out and emerges after a further reflection from the light-conductive film. A further barrel lens Z2 is mounted spaced away from the focal point by the focal length so that subsequently a parallel beam path is reachieved. The deviating mirror 2 (UL2) and an optical assembly of lenses L4, L5 images the distribution of the intensity as present in the plane of the barrel lens 2 on a detector, e.g. a CCD chip (Det). This results in an image materializing on the CCD chip (Det) in which in the vertical direction the angular spectrum is imaged and in the direction pointing into the plane of the drawing the various sensor sites of the sensor are imaged juxtaposed. Although this configuration only makes it possible to assay one discrete sensor in parallel, the advantage thereof is the shorter time needed therefor so that e.g. kinetic experiments can be carried out. A two-dimensional array could be characterized line-by-line in sequence with this assembly by shifting it through the focal point of the optical sensing assembly by means of a mechanical shifting system.

Assemblies for scanning SPR sensors or arrays in parallel are described in German patent DE 199 55 556.7 to the disclosure content of which in this respect reference is made herewith and whose content is included by reference thereto.

Figure 8:
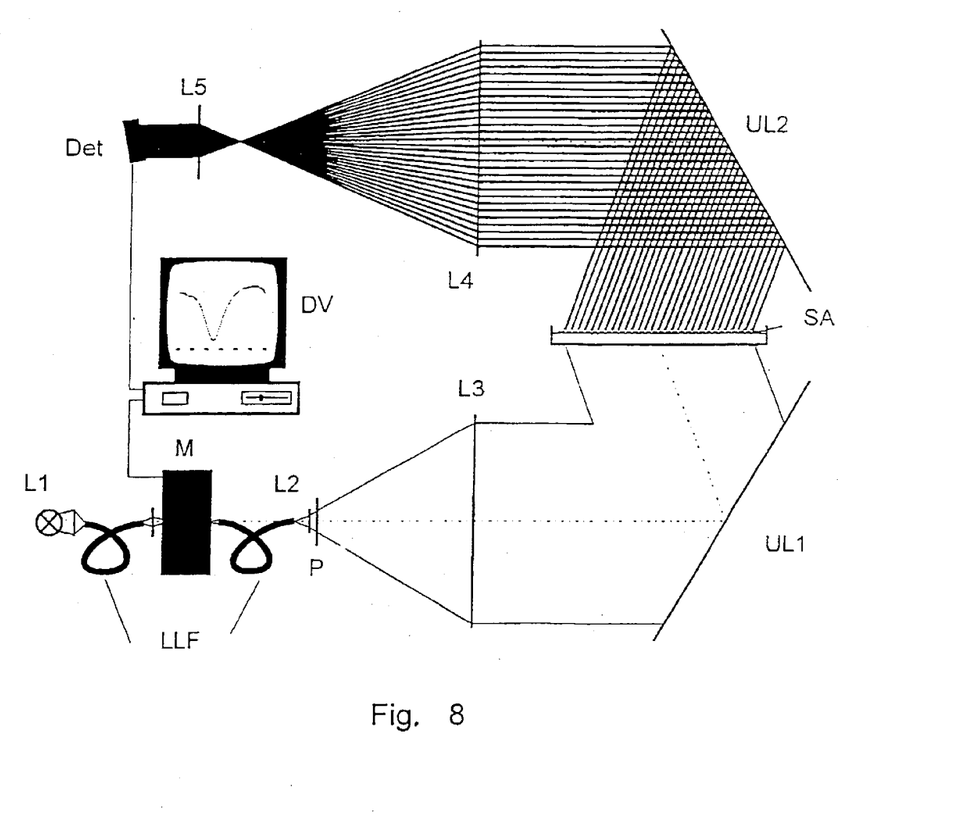

Referring now to FIG. 8 there is illustrated an assembly working in accordance with the principle of a parallel beam path within the sensor (the same as in FIG. 2). In this case, the light of a halogen lamp is communicated through an optical fiber (LLF) to the monochromator (M) and through a further optical fiber for beam spreading (lenses L2, L3). By means of the polarizer (P) TM polarization as regards the reflection at the sensor film is selected. The sensor array (SA) is exposed by a spread parallel beam at an angle of incidence at which resonance is anticipated.

At the upper end of the sensor (see also FIG. 2) the light exits offset only parallel (FIG. 2b) either at the same angle at which it entered below (for an even number of reflections) or at the negative angle (for an odd number of reflections—see FIG. 2a). The height H and thickness D of the SPR sensor are then dimensioned so that the number of reflections is odd, resulting in only the negative angle occurring and thus the light exiting at the top right (FIG. 8).

In the further beam path the exposure light path is practically the reverse: via a large-diameter collimating lens L4 and an objective lens L5 the surface area of the sensor array is imaged on the CCD chip (Det) in a telescopic imaging arrangement. Since the surface of the sensor array to be imaged is not located perpendicular to the optical axis of the arrangement, only a line of the objective is crisply imaged due to the inadequate depth of focus with a conventional camera in which the objective lens is located parallel to the CCD chip (Det). This is why at the imaging side the CCD chip (D) likewise needs to be tilted relative to the optical axis to ensure a crisp image of the complete sensor array surface area. This is achieved by tilting the CCD camera (D) with a goniometer relative to the objective lens (L5).

The image of the sensor array is communicated to the processor DV which has the role of a central controller, and each sensor site is assigned an intensity value by the integral thereof being formed in an image range assigned to the sensor site. In a new setting of the wavelength a further such image is detected and analyzed in thus successively obtaining a complete spectrum for each sensor site. At the wavelength satisfying the condition for resonance, there is a drop in the detected intensity, due to energy of the light being converted into plasmon excitation, termed "SPR dip". The wavelength at minimum intensity can be determined numerically as is characteristic for the refractive index of the fluid on the gold film.

Refractive index and density are the same for most proteins and thus the refractive index of the medium on the gold film is directly proportional to the mass coating density.

The molecular association of each SPR sensor is not given by the absolute intensity spectrum of a discrete measurement but by the shift in the wavelength at the minimum for a measurement in the buffer solution alone as compared to the minimum of a second measurement in the presence of the targeted molecule. It is not until this difference is obtained that an indication as to the molecular association is possible.

When using focused light, as evident from FIG. 7, the optical system as shown in FIG. 8 needs to be supplemented by the lenses Z1 and Z2 in the beam path. These serve to focus the light beam on a point or line where the angular function of the SPR effect is used for characterizing the solution.

Although the measuring assemblies as shown in FIGS. 7 and 8 related to transmission measurement (see also FIGS. 2a and 2b) it will readily be appreciated that these assemblies are basically just as suitable too for reflection measurement (see also FIG. 2c). For this purpose it is to be noted that entrance and exit surface areas for the light are the same so that the optical system for analyzing the results needs to be arranged accordingly. Using a reflection measurement has the advantage that the light does not need to pass through the fluid being assayed.

The sensors or arrays thereof in accordance with the invention find application in the search for active agents and in high-throughput screening.

EXAMPLE

The following explains how a sensor as shown in FIG. 6 is produced by way of example.

Use is made of a strip of borosilicate in a thickness of 0.7 mm. The height of the glass strips of 17 mm is dimensioned so that precisely three reflections are allowed when irradiated with parallel light at an angle of 83°.

Both ends into and from which the parallel light is coupled are polished. The width of the strips is 78 mm. On a center-spacing of 2.25 mm 33 cut-outs each 1 mm wide and 6 mm deep are cut into the glass strips by means of a glass saw. These cut-outs result in comb-like strips having 32 "fingers" or teeth which then serve as sensor sites.

Once these fingers have been structured, the individual glass strips are coated with an adhesive film so that, except for a finger length of 6 mm, the complete glass strip is covered. In a subsequent coating process it is thus only the lower 6 mm of the fingers that receive the SPR-sensitizing gold film, the rest of the glass remaining unaffected by the coating process. The covering is then removed after coating. A roughly 1 nm thick film of chromium is deposited prior to coating to promote bonding. The gold film then applied has a thickness of approx. 35 nm.

What is claimed is:

1. A sensor for surface plasmon resonance (SPR) spectroscopy for parallel assaying a plurality of samples, comprising a body including a plurality of SPR sensor sites for guiding radiation in SPR assaying and coated with a suitable SPR-sensitizing material, and separating means which separate the SPR sensor sites by separating the SPR-sensitizing coating so that each SPR sensor site is assignable to one sample only, characterized in that the body conducts the radiation in forming with the SPR sensor sites a unit so that the beam path of the radiation guided through the SPR sensor sites also passes through the radiation-conductive body.

2. The SPR sensor as set forth in claim 1, characterized in that the body and the SPR sensor sites are made from one and the same radiation-transparent substrate.

3. The SPR sensor as set forth in claim 1, characterized in that the SPR sensor sites and separating means are components of the body and make up together at least part of the body.

4. The SPR sensor as set forth in claim 3, characterized in that the body is composed of a full-length planar radiation conductor, and the SPR sensor sites are defined by first surface areas on a surface of the body consisting of SPR-sensitizing material, and the separating means are defined by second surface areas located between the surface areas of SPR-sensitizing material on the same and/or opposite surface of the body and are composed of a second material suitable for extinction of the radiation in the radiation conductor between the SPR sensor sites.

5. The SPR sensor as set forth in claim 4, characterized in that the second surface areas are configured on the same surface of the body as the first surface areas and the second surface areas forms fluid barriers between neighboring first surface areas.

6. The SPR sensor as set forth in claim 4, characterized in that the first and second surface areas are configured as strips, the first strips all being parallel and equispaced from each other, and the center-spacing between neighboring first strips is in the range 0.01 to 10 mm, preferably 0.1 to 1 mm.

7. The SPR sensor as set forth in claim 1, characterized by finger-shaped protuberances comprising SPR sensor sites, and cut-outs which form separating means between the cut-outs.

8. The SPR sensor as set forth in claim 7, characterized in that the finger-shaped protuberances are divided into sensor sites and the separating means between the sensor sites are formed by further cut-ours and/or by coated sites on the surface of the protuberances.

9. The SPR sensor as set forth in claim 7, characterized in that the protuberances correspond to the SPR sensor sites in protruding parallel and equispaced in forming together with body a comb-like structure.

10. The SPR sensor as set forth in claim 9, characterized in that the SPR sensor sites have the center-spacing of a multiwell plate matrix.

11. The SPR sensor as set forth in claim 1, characterized in that the radiation is light in the infrared or visible range.

12. The SPR sensor as set forth in claim 1, characterized in that the body and the SPR sensor sites are made of glass or a polymer.

13. The SPR sensor as set forth in claim 12, characterized in that the body and the SPR sensor sites are made of borosilicate glass.

14. The SPR sensor as set forth in claim 1, characterized in that between the SPR sensor sites, and the SPR-sensitizing material in each case an interfilm, preferably of chromium or titanium is provided to promote bonding.

15. The SPR sensor as set forth in claim 1, characterized in that the SPR-sensitizing material is a metal, preferably, platinum, gold, silver, aluminum, copper, nickel or an alloy of two or more of these metals.

16. The SPR sensor as set forth in claim 1, characterized in that the body, and the SPR sensor sites comprise a refractive index in the range 1.46 to 1.58 and uses gold as the SPR-sensitizing material.

17. The SPR sensor as set forth in claim 1, characterized in that the SPR sensor sites comprise a cross-sectional dimension in the range 0.1 mm to 5 mm.

18. An SPR sensor array comprising a plurality of SPR sensors each comprising: a body including a plurality of SPR sensor sites for guiding radiation in SPR assaying and coated with a suitable SPR-sensitizing material, and separating means which separate the SPR sensor sites by separating the SPR-sensitizing coating so that each SPR sensor site is assignable to one sample only, characterized in that the body conducts the radiation in forming with the SPR sensor sites a unit so that the beam path of the radiation guided through the SPR sensor sites also passes through the radiation-conductive body, the SPR sensors being configured planar and all arranged planoparallel.

19. The SPR sensor array as set forth in claim 18, characterized in that the SPR sensors at a radiation exit surface area or radiation entrance surface area are connected to a surface of a covering plate transparent to the radiation, and at the opposite surface of the plate a mask is provided comprising radiation windows arranged to permit passage of radiation from the SPR sensor sites or into the SPR sensor sites of the discrete SPR sensors.

20. The SPR sensor array as set forth in claim 18, characterized in that the neighboring SPR sensors are separated by intermediate elements, each of which is connected to the corresponding neighboring SPR sensor sites.

21. The SPR sensor array as set forth in claim 20, characterized in that the intermediate elements are configured to permit no exit of radiation at the side of the SPR sensor array at which radiation exits from the sensor sites of the SPR sensors.

22. The SPR sensor array as set forth in claim 20, characterized in that the each intermediate element, comprises at least one first part connected to the neighboring SPR sensor in defining the spacing between said neighboring SPR sensors, and a second part leaving a free spacing between neighboring SPR sensors through which a fluid can flow, openings being provided in the second part which expose SPR-sensitized coated surface areas of SPR sensor sites of one of the SPR sensors so that fluid flowing through the free space can come into contact with the SPR-sensitized coated surface areas of SPR sensor sites of one of the SPR sensors.

23. The SPR sensor array as set forth in claim 22, characterized in that the plurality of SPR sensors and intermediate elements are arranged so that the discrete free spaces between neighboring SPR sensors form a meander-shaped flow path.

24. The SPR sensor array as set forth in claim 18, characterized in that 10 to 100,000 SPR sensor sites are included.

25. A method of producing a SPR sensor each comprising: a body including a plurality of SPR sensor sites for guiding radiation in SPR assaying and coated with a suitable SPR-sensitizing material, and separating means which separate the SPR sensor sites by separating the SPR-sensitizing coating so that each SPR sensor site is assignable to one sample only, characterized in that the body conducts the radiation in forming with the SPR sensor sites a unit so that the beam path of the radiation guided through the SPR sensor sites also passes through the radiation-conductive body, comprising the steps:

coating first surface areas on a surface of a planar radiation-conductive substrate with the SPR-sensitizing material to define the SPR sensor sites in the substrate, applying elevations of a second material to second surface areas located between the first surface areas to form the separating means, the second material being such that the radiation in the substrate in areas between the SPR sensor sites is blocked, and the elevations have a height from the substrate surface, that to each SPR sensor site only a single sample is assignable by each elevation forming a fluid barrier for the fluids to be assayed with the SPR sensor, scheduling the step of coating the first surface areas before or after the step of applying the second material.

26. The method as set forth in claim 25, characterized in that first the elevations are formed on the second surface areas and the SPR-sensitizing material is applied thereafter to the first surface areas in making use of the elevations on the second surface areas as a mask.

27. The method as set forth in claim 25, characterized in that the elevations of the second material are produced with the aid of a mask.

28. The method as set forth in claim 27, characterized in that the mask is a screen-printed mask, a photopatterned resist, or a prepatterned cover added to the surface of the substrate.

29. A method of producing a SPR sensor as set forth in claim 1, comprising the steps: coating first surface areas on a surface of a planar radiation-conductive substrate with the SPR-sensitizing material to define the SPR sensor sites in the substrate, forming recesses between the SPR sensor sites to form the separating means, scheduling the step of coating the first surface areas before or after the step of forming the recesses.

30. The method as set forth in claim 29, characterized in that forming the recesses is done by sawing and/or milling and/or etching the radiation-conductive substrate.

31. The method as set forth in claim 25, characterized in that the substrate is made of glass or a polymer.

32. The method as set forth in claim 31, characterized in that the substrate is made of borosilicate.

33. The method as set forth in claim 25, characterized in that the step of coating the first surface areas involves depositing a bond-promoting interfilm, preferably of titanium or chromium between the substrate and the SPR-sensitizing material.

34. The method as set forth in claim 25, characterized in that the SPR-sensitizing material is a metal, preferably platinum, silver, aluminum, copper, nickel, gold or an alloy of two or more of these metals.

35. The method as set forth in claim 25, characterized in that the substrate has a refractive index in the range 1.46 to 1.58 and gold is used as the SPR-sensitizing material.

36. The method as set forth in claim 25, characterized in that the SPR sensor sites feature a cross-sectional dimension in the range 0.1 mm to 5 mm.

37. The method for producing a SPR sensor array as set forth in claim 18, comprising the steps: connecting the light entry surface areas or light exit surface areas of the discrete SPR sensors to a surface of a radiation-transmissive plate, applying a radiation cover to the opposite surface of the plate comprising radiation windows arranged so that passage of radiation from the SPR sensor sites or into the SPR sensor sites is permitted.

38. The method as set forth in claim 37, characterized in that connecting the SPR sensors to the plate is done by means of a transparent adhesive having preferably a refractive index differing from that of the plate and/or of the SPR sensors by maximally 10%.

39. The method for producing a SPR sensor array as set forth in claim 18, comprising the step of connecting the discrete SPR sensors by intermediate elements, each of which is connected to two neighboring SPR sensors.

40. The method as set forth in claim 39, characterized in that the intermediate elements are connected to the SPR sensors by means of an adhesive and the refractive index of the adhesive and/or of the intermediate elements is smaller than the refractive index of the SPR sensors.

41. A measuring assembling for surface plasmon resonance spectroscopy permitting simultaneously assaying of a plurality of samples, comprising a SPR sensor comprising: a body including a plurality of SPR sensor sites for guiding radiation in SPR assaying and coated with a suitable SPR-sensitizing material, and separating means which separate the SPR sensor sites by separating the SPR-sensitizing coating so that each SPR sensor site is assignable to one sample only, characterized in that the body conducts the radiation in forming with the SPR sensor sites a unit so that the beam path of the radiation guided through the SPR sensor sites also passes through the radiation-conductive body or a SPR sensor array comprising a plurality of SPR sensors each comprising: a body including a plurality of SPR sensor sites for guiding radiation in SPR assaying and coated with a suitable SPR-sensitizing material, and separating means which separate the SPR sensor sites by separating the SPR-sensitizing coating so that each SPR sensor site is assignable to one sample only, characterized in that the body conducts the radiation in forming with the SPR sensor sites a unit so that the beam path of the radiation guided through the SPR sensor sites also passes through the radiation-conductive body, the SPR sensors being configured planar and all arranged planoparallel, a radiation source for emitting radiation of a wavelength suitable for SPR assaying, a radiation focusing means for forming convergent radiation from the radiation emitted by the radiation source, the convergent radiation being guided so that it enters at least two difference SPR sensor sites of the SPR sensor array via separate entrance windows of the SPR sensor sites, and radiation focusing means and SPR sensor sites are arranged so that the focal point of the convergent radiation is located on the surface of the SPR sensor sites coated with SPR-sensitizing material to be reflected by said surface, and a radiation analyzing means to detect and analyze the reflected radiation.

42. The measuring assembly as set forth in claim 41, characterized in that the entrance windows of the SPR sensor sites and the covergent radiation are oriented so that the center beam of the covergent radiation suffers no refraction on entering the SPR sensor site.

43. The measuring assembly as set forth in claim 41, characterized in that the exit windows of the SPR sensor sites and the covergent radiation are oriented so that the center beam of the covergent radiation suffers no refraction on exit from the SPR sensor site.

44. The measuring assembly as set forth in claim 41, characterized in that the radiation focusing means comprises a barrel lens arranged together with the SPR sensor array so that the convergent radiation formed by the barrel lens enters simultaneously all SPR sensor sites of the SPR sensor or one SPR sensor of the SPR sensor array.

45. The measuring assembly as set forth in claim 44, characterized in that a SPR sensor array is provided, and that a shifting means is provided configured to shift the SPR sensor array so that one SPR sensor after the other can be assayed.

46. A measuring assembly for surface plasmon resonance spectroscopy permitting simultaneously assaying of a plurality of samples, comprising a SPR sensor comprising: a body including a plurality of SPR sensor sites for guiding radiation in SPR assaying and coated with a suitable SPR-sensitizing material, and separating means which separate the SPR sensor sites by separating the SPR-sensitizing coating so that each SPR sensor site is assignable to one sample only, characterized in that the body conducts the radiation in forming with the SPR sensor sites a unit so that the beam path of the radiation guided through the SPR sensor sites also passes through the radiation-conductive body, or a SPR sensor array (SA) comprising: a plurality of SPR sensors each comprising: a body including a plurality or SPR sensor sites for guiding radiation in SPR assaying and coated with a suitable SPR-sensitizing material, and separating means which separate the SPR sensor sites by separating the SPR-sensitizing coating so that each SPR sensor site is assignable to one sample only, characterized in that the body conducts the radiation in forming with the SPR sensor sites a unit so that the beam path of the radiation guided through the SPR sensor sites also passes through the radiation-conductive body, the SPR sensors being configured planar and all arranged planoparallel, a radiation source for emitting radiation of a wavelength suitable for SPR assaying, a radiation parallelizing means for forming parallel radiation, a radiation guidance means for guiding the parallel radiation arranged together with the SPR sensor array so that the parallel radiation impinges at least two of the SPR sensor sites of the SPR sensor array in such a way that the parallel radiation enters via each of the radiation entry windows into the SPR sensor sites and is guided therein so that it is reflected by the surface of the SPR sensor sites coated with the SPR-sensitizing material, and a radiation analyzer means for detecting and analyzing the reflected radiation.

47. The measuring assembly as set forth in claim 46, characterized in that the radiation guidance means and SPR sensor or SPR sensor array (SA) are arranged so that the parallel radiation impinges all SPR sensor sites of the SPR sensor or of the SPR sensor array (SA).

48. The measuring assembly as set forth in claim 46, characterized in that the radiation analyzer means comprises an imaging optical assembly and a detector, the imaging optical assembly imaging the reflection radiation on the detector and the detector permitting spatial resolution of the radiation stemming from the discrete SPR sensor sites.

49. The measuring assembly as set forth in claim 48, characterized in that the radiation analyzer means comprises a means for tilting the detector relative to the optical axis of the imaging optical assembly.

50. The measuring assembly as set forth in claim 49, characterized in that the means for tilting the detector is a goniometer.

51. The measuring assembly as set forth in claim 48, characterized in that the detector comprises a CCD chip.

52. The measuring assembly as set forth in claim 46, characterized in that a control unit is provided connected to the radiation source and to the radiation analyzer means and configured so that the wavelength of the radiation emitted by the radiation source can be adjusted by the control unit which permits detection and storage of the intensity of the radiation stemming from the SPR sensor sites, the intensity being detected as a function of the set wavelength by the radiation analyzer means.

* * * * *

UNITED STATES PATENT AND TRADEMARK OFFICE
CERTIFICATE OF CORRECTION

PATENT NO. : 6,795,192 B2
DATED : September 21, 2004
INVENTOR(S) : Dickopf et al.

It is certified that error appears in the above-identified patent and that said Letters Patent is hereby corrected as shown below:

Column 14,
Line 36, after "with" add -- the --.

Column 18,
Line 11, change "or" with -- of --.

Signed and Sealed this

Fifth Day of April, 2005

JON W. DUDAS
*Director of the United States Patent and Trademark Office*